United States Patent [19]
Galun et al.

[11] Patent Number: 4,732,681
[45] Date of Patent: Mar. 22, 1988

[54] REMOVAL OF CONTAMINANTS

[75] Inventors: Margalith Galun; Esra Galun, both of Rehovot, Israel

[73] Assignee: Ramot University Authority for Applied Research and Industrial Development Ltd., Ramat, Israel

[21] Appl. No.: 857,140

[22] Filed: Apr. 29, 1986

[30] Foreign Application Priority Data

May 2, 1985 [IL] Israel ......................................... 75073

[51] Int. Cl.$^4$ .......................... C02F 3/32; C12R 1/645
[52] U.S. Cl. .................................... 210/611; 210/601; 210/688; 210/912; 435/264; 435/911
[58] Field of Search ............... 435/171, 254, 264, 911; 210/912, 688, 611, 601

[56] References Cited

U.S. PATENT DOCUMENTS 4,505,821  3/1985  Kaneko et al. ....................... 435/254

FOREIGN PATENT DOCUMENTS

| 57-136997 | 8/1982 | Japan | 210/601 |
| 895930 | 1/1981 | U.S.S.R. | 210/601 |
| 969684 | 10/1982 | U.S.S.R. | 210/601 |
| 1063834 | 12/1983 | U.S.S.R. | 435/911 |

OTHER PUBLICATIONS

*International Symposium on Metal Speciation, Separation and Recovery*, Jul.-Aug. 1986.
Discussion of "*Fungal Biosorption: A Comparative Study of Metal Uptake by Pencillium and Cladosporium*", Paul R. Anderson.

Primary Examiner—Benoît Castel
Attorney, Agent, or Firm—Oblon, Fisher, Spivak, McClelland & Maier

[57] ABSTRACT

Heavy elements such as Pb, Zn, Cd, Ni, Cu and Cr constitute health hazards and are sources for environmental pollution. These elements should therefore be removed from industrial effluents. Biomass of *Cladosporium cladosporioides* (Fresen.) de Vries. Acc. No. 285712 is readily produced by culture in either standard fungal medium or on media composed of food-industry wastes: whey and distillery slop. The thus produced fungal biomass efficiently removes heavy elements from liquid solutions. Removal is achieved from fluids containing single heavy elements as well as from fluids containing two or more such elements. The removal of Cr can be vastly improved by Pb pretreatment of the biomass. Elements absorbed by *Cladosporium cladosporioides* Acc. No. 285712 are quantitatively removable providing an effluent-cleaning system which is renewable.

10 Claims, 2 Drawing Figures

REMOVAL OF CONTAMINANTS

FIELD OF THE INVENTION

There are provided novel means for the removal of, or for the substantial reduction of the concentration of heavy metal contaminants in aqueous waste liquors or effluents. The removal is based on the adsorption of such heavy metals by means of a fungal hyphae biomass of the fungal organism *Cladosporium cladosporioides* (Fresen) de Vries, Acc. No. 285712, Commonwealth Mycological Institute, Surrey, United Kingdom. There is provided a process for the removal of such heavy metals and also a process for the production of such active biomass. The adsorbed heavy metals can be desorbed, and thus the biomass can be reconstructed for further adsorption processes. The fungi can be produced in an efficient and inexpensive manner by cultivation on a medium comprising mainly industrial wastes.

BACKGROUND OF THE INVENTION

The ability of microorganisms to biosorb elements such as uranium ($U^{+6}$) and other elements is well documented in the literature (see Galun et al., Science 219, 285, 1983; Tsezos and Volesky, Biotechnology and Bioengineering 23, 583, 1981; Tsezos and Keller, Biotechnology and Bioengineering, 25, 201, 1983, Tobin et al. Appl. and Environ. Microbiol. 47, 821, 1984). Microorganisms-derived products were also shown to have a metal-biosorption capability (Galun et al., Science 219, 285, 1983; Tsezos, Biotechnology and Bioengineering 25, 2025, 1983; Zosim et al., Biotechnology and Bioengineering 25, 1725, 1983).

The quantitative removal of elements from fungal biomass is also documented (Galun et al., Water, Air and Soil Pollution 20, 277, 1983).

Although bacteria can absorb heavy metals (Beveridge, Can. J. Microbiol. 24, 89, 1981; DiSpritio et al., Arch. Microbiol. 135, 250, 1983) and their use to remove metal ions from aqueous process streams was suggested (Shumate et al, Biotech. Bioengineering Symp. (Oak Ridge) 8, 13, 1978), their biosorption capacity is far lower than that of fungal organisms and the production of the respective microorganisms requires expensive culture media.

The reported results on fungal-mass biosorption of elements were based on Penicillium sp: and *Rhizopus arrhizus* and did not relate to the efficiency of fungal biomass production neither was it attempted to preculture these fungal organisms on low cost organic waste products. In no case was the fungal organism *Cladosporium cladosporioides*, which is a non-pathogenic soil saprophyte, used or suggested as source for fungal biomass to serve in removal of elements from contaminated effluents.

SUMMARY OF THE INVENTION

There are provided means for the efficient removal of heavy metal contaminants from aqueous waste liquors of various industries. The removal is effected by means of a fungal biomass comprising mainly hyphae of the fungus *Cladosporium cladosporioides* (Fresen) de Vries, Acc. No. 285712 (Commonwealth Mycological Institute, having a business address at: Ferri Lane, Kew, Richmond, Surrey, TW9 3AF, United Kingdom). The heavy metals are removed by biosorption on the biomass, and can be removed to a large extent. The starting aqueous effluents contain such contaminants generally in concentrations of the order of some ppm, up to some tens of ppms and it is generally required to reduce such concentrations to the order of less than 1 ppm. The fungal mass can be obtained by the cultivation on an inexpensive culture medium, such as 10 to 20% distillery slop and about 1 to 2% whey powder, with about 0.1% $NH_4NO_3$. No additional organic or inorganic additives are required. The biomass can be harvested after a period of the order of 5 to 10 days, and the hyphal mass can be used by contacting same with the aqueous medium from which the heavy metal or metals are to be removed. There is also provided a process for the removal of heavy metals from aqueous waste liquors. There is also provided a process for the regeneration and repeated use of the biomass. The process is especially applicable to Ni, Cu., Zn, Cd, Pb and Cr or mixtures of any of these. For the removal of chromium, preconditioning of the biomass with lead is highly advantageous.

The fungal organism *Cladosporium cladosporioides* (Fresen.) de Vries, Acc. No. 285712 (the organism of this invention) excells, relative to other related fungal organisms by its lack of spore production when cultured in liquid media thus providing a virtually pure yield of hyphae which are the actual biosorbents of elements. Furthermore several other Cladosporium accessions, isolated from natural habitats, were active, but inferior to *C. cladosporioides* Acc. No. 285712, in respect to element-biosorption.

The organism of this invention can be grown in low-cost media composed of 10 to 20% distillery slop, 1 to 2% whey powder (or the equivalent in liquid whey) and 0.1% $NH_4NO_3$, without the addition of any other organic or mineral supplement. Alternatively, when the above mentioned food-industry wastes are not available standard fungal culture media can be used. Sucrose can substitute for whey.

The culture does not require pH adjustment and the fungal-biomass yields 150 g (or more) wet-weight (or 13 g or more dry-weight) of biomass per liter culture medium, during 7 days of culture.

The biomass of the organisms of this invention can thus be furnished in either shake cultures, aerated-carboy cultures or standard fungal fermentors. In either of these, cultures are seeded with an appropriate inoculm from a stock culture. To maintain the fungal biomass in the form of discrete (but not tight) hyphal beads, Tween 80, up to 0.5% and up to 0.1% of $NH_4NO_3$ should be added to the medium before begin of culture.

At the termination of the culture process further growth can be terminated by any of the common ways of the art, e.g. heating to 95° C., exposure to sodium azide or the biomass is harvested without killing.

The biomass may be harvested by a variety of means, such as filtering over a screen, or centrifugation. It is then water-washed and freed from surplus water by common procedures. The biomass is then ready to be used for element biosorption. It can be used immediately or it can be stored for up to several weeks at 2° to 4° C. and used as required.

Element biosorption is effected by either of several procedures. In batch containers 200 g W.W. (about 16 g D.W.) of biomass is added to each liter of element containing effluent for 30 to 120 minutes. The length of the processing time depends on the element to be removed. About 30 minutes is sufficient for uranium and lead, but 120 minutes are required for effluents containing chromium, nickel, zinc and cadmium. The biomass is then separated from the liquid and the biosorbed element can be removed by washing with a solution containing 15 g $Na_2CO_3$ and 5 g $NaHCO_3$ or with 0.1% $HNO_3$. The biomass can then be completely rejuvenated with a 0.01N NaOH wash. The process of removal and rejuvenation can be repeated 5–7 times. In the case of chromium this element can be removed by washing with a 0.01N NaOH solution, the fungal biomass then regenerated with a 0.1% $HNO_3$ solution wash and the process repeated 5–7 times. For effluents containing up to 5 ppm of element one biosorption treatment should reduce the element level to below the hazardous level. For element concentration of 5–20 ppm the process is repeated with either new biomass or with rejuvenated biomass, until the effluent is fully decontaminated. Effluents containing even higher element concentrations, e.g. 100 ppm or more, are decontaminated by repeating this process several times.

For elements which have a quick biosorption kinetics, such as uranium and lead, a filter system can be employed in which the biomass of the organism of this invention is packed in columns and the effluent is filtered through the biomass. The flow-rate and the number of filter passages are adjusted to the level of contaminating elements in the effluent.

The biosorption capacity of the organism of this invention towards chromium can be substantially increased by pretreatment of the biomass with lead, with a $Pb(NO_3)_2$ solution. For this procedure the biomass is placed in a column and a volume of a 100 ppm solution of $Pb(NO_3)_2$ filling the void of the column is passed through the columns.

The biomass is then washed twice with water before its use to biosorb chromium from aqueous solutions. Alternatively, the biomass is placed in a container and X5 volumes of 100 ppm $Pb(NO_3)_2$ are added. After 10 minutes the $Pb(NO_3)_2$ is removed, replaced with water and the water is removed after 5 minutes. The water wash is repeated twice before the Pb coated biomass is used for chromium biosorption.

BRIEF DESCRIPTION OF THE DRAWINGS

The invention is illustrated with reference to the enclosed Figures, wherein.

DESCRIPTION OF THE PREFERRED EMBODIMENTS

Figure 1:
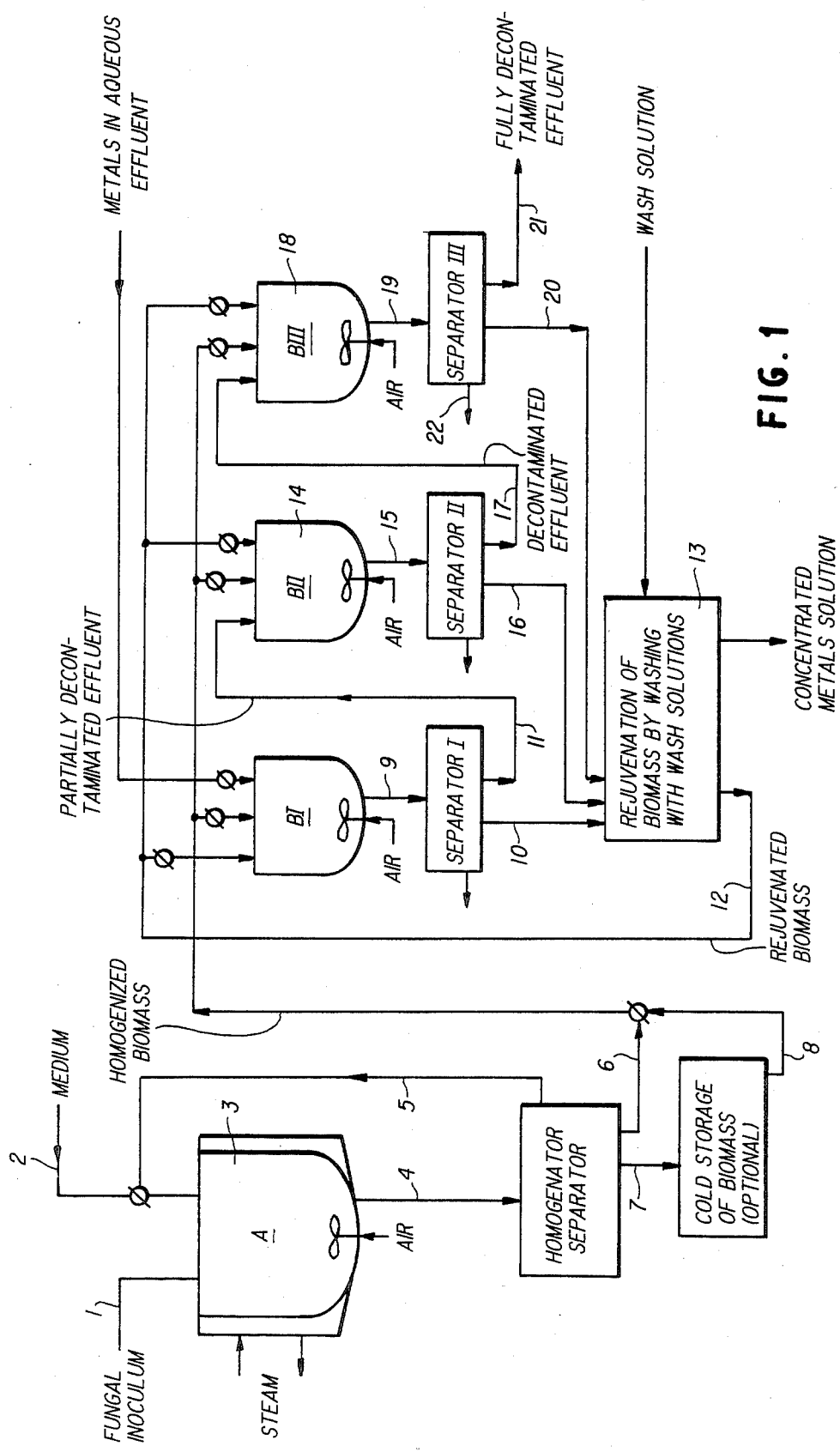
FIG. 1 is a schematical layout of a multiphase biosorption system for the removal of contaminants.

A system for the removal of impurities from effluents is described in FIG. 1. This is by way of illustration only. As illustrated in the drawing, FIG. 1, fungal inoculum is fed (1) into an incubation tank (A) which is surrounded by a steam (or water) jacket which allows (optional) heat-killing of the fungal mycelium after biomass is produced. Medium (12) containing 10 or 20% distillery slop, 1% whey powder, 0.1% $NH_4NO_3$ and 0.5% Tween 80 or a medium composed of other available low-cost ingredients or any other medium suitable for *Cladosporium cladosporiodes* biomass production, is pumped into the tank (3) and biomass production is achieved within 3 or more days at desired temperature. The fungal biomass is then led (4) into a homogenator/separator. From there, the biomass slurry is either recycled (5) to incubation tank (A) or is led (7) to cold storage for future use or the biomass is transferred directly (6) to one or more of the element/biomass incubation tanks (BI, BII, BIII) equipped with a mechanism that assures thorough mixing of the biomass with metal containing effluents. The element-containing effluent is fed into tank BI and incubation is maintained for 10, 30 or 120 minutes according to the element in the effluent. Elements as U and Pb require short incubation while Ni and Zn require 120 minutes.

After incubation the content of tank BI is transferred (9) to separator I. From there the biomass is transferred (10) to a washing tank (13) and the partially decontaminated effluent is fed (11) into the second element/biomass incubation tank BII. In the washing tank (13) the metal is released from the biomass by washing with a wash solution. Such washing solutions 15 g $Na_2CO_3$ and 5 g $NaHCO_3$ per liter, for release of some metals as Pb and U, or are composed of hydrochloric or nitric acid. The biomass can be rejuvenated by NaOH wash and water wash, and reintroduced (12) into one of the element/biomass incubation tanks (BI, BII, BIII). In the case of Cr-removal, this is stripped by NaOH followed by $HNO_3$ or HCl wash. Tank BII is operated (14) by incubating the partial decontaminated effluent with either fresh or rejuvenated biomass for 10, 30 or 120 minutes according to the elements in the effluent. Thereafter, the content of tank BII is processed (15) as described for the content of tank BI and the cycle may be proceeded for a third decontaminating incubation in tank BIII, by releasing the content of BII into separator II and from there the biomass is fed (16) to the washing tank (13) and the decontaminated effluent is fed (17) to tank BIII for a third element/biomass incubation (18). After the last incubation the content of tank BIII is led (19) to separator III, the biomass is transferred (20) to the washing tank (13) and the fully decontaminated effluent is released (21).

The process is flexible in the way that if the level of element in the effluent is low and the element being efficiently biosorbed by the biomass, as is in the case of Pb, one or two cycles of element/biomass incubations will suffice to recover fully decontaminated effluent. Furthermore biomass production can be maintained as a separate operation to supply biomass when needed. When the biosorption capacity of the biomass of a B tank deteriorates in spite of rejuvenation it can be discarded (22) after separation and replaced by fresh biomass (8) or by another batch of rejuvenated biomass (12).

EXAMPLE 1

Fungal-Biomass Production

Ehrlenmyer flasks (0.5 l) were filled with 200 ml of liquid culture media. Potato-dextrose (Difco), a standard fungal medium, served as control. Other media contained several combinations of distillery slop, whey and sucrose. The culture media contained 0.5% Tween 80. The flask were incubated with either *Cladosporium cladosporioides* Acc. No. 285712 or *Penicillium digitatum* (control) stock cultures, put on a rotating shaker (160 rpm) and maintained at 25°±2° C. up to harvest. After 3 or 7 days in culture the mycelium was harvested by filtering over a nylon screen and water-washed. Wet weight and dry-weight determinations were by standard procedures. Table 1 provides data on the biomass production during 3 and 7 days incubation. Distillery slop with either sucrose or whey provided suitable media for *C. cladosporioides* but not for *P. digitatum*. Furthermore biomass of *C. cladosporioides* increased substantially during the period following the third day in culture providing a two-fold increase of biomass to medium-input relative to *P. digitatum*.

EXAMPLE 2

Removal of Elements by Precultured Biomass

Aqueous solutions of the elements Ni, Cu, Zn, Cd, Pb and Cr were prepared from $NiCl_2$, $CuSO_4$, $ZnCl_2$, $CdCl_2$, $Pb(NO_3)_2$, and $K_2Cr_2O_7$, respectively. Aliquots of 10 g (D.W.) *C. cladosporioides* Acc. No. 285712 biomass, prepared as described in Example 1, were added to each liter of element solution. The suspensions were incubated at 25°±2° C. without pH adjustment. After 10, 30 or 120 minutes the solutions and the biomass were separated and samples of the solution were analyzed for element content determination. The solutions were reincubated once or twice with biomass and samples of it were analyzed for element content. The results in Table 2 detail the elements content in the solution after the first incubation (for 10, 30 and 120 minutes) and indicate how many cycles with a certain incubation time, were required to remove the elements from the solution to beyond detection by AAS which was less than 0.1 ppm. In addition to the results presented in Table 2, 25 ppm $Pb(NO_3)_2$ was also incubated for 10, 30 or 120 minutes and the concentrations which were measured in the solution at the end of incubation were 5.0, 0.75 and 0.1 ppm respectively. Thus even 25 ppm $Pb(NO_3)_2$ could virtually be removed with one incubation of 120 minutes.

EXAMPLE 3

The Kinetics of Element Biosorption

Figure 2:
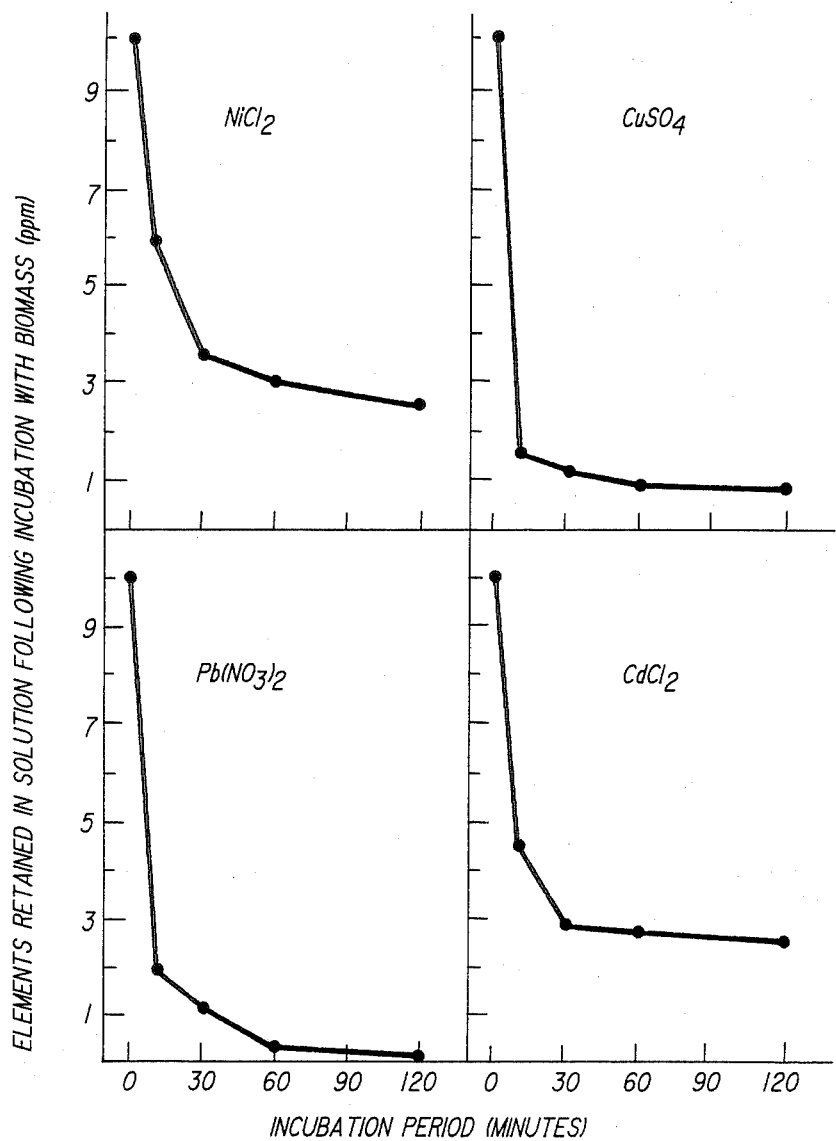
FIG. 2 illustrates the kinetics of biosorption of nickel, copper, lead and cadmium by *Cladosporium cladosporioides*.

Aqueous solutions were prepared as in Example 2 and 10 ppm solutions were incubated with equivalents of 10 g fungal biomass per 1 liter solution. Batches of solutions with biomass were removed for elements-content analysis at the beginning and 10, 30, 60 and 120 minutes after beginning of incubation. Results are presented in FIG. 2.

EXAMPLE 4

Interaction Between Elements

Aqueous solutions of elements were prepared as in Examples 2 and 3. For each of the elements Pb, Cu, Zn, Cd and Ni, solutions were prepared which contained 5, 10 or 20 ppm of that element as well as 0,5, 10 or 12 ppm of one of the other four elements. Equivalents of 10 g biomass per 1 liter were added to each of these solutions and incubation was as in Examples 2 and 3. Two hours after beginning of incubations the metal content in the liquid was analyzed as in Example 2. Table 3 demonstrates two interactions. In one: biosorption of Cu in the presence of Pb, there was no reduction of biosorption even in the presence of 20 ppm $Pb(NO_3)_2$. In the second, the biosorption of the Zn in the presence of $CdCl_2$ there was a slight reduction of Zn removal from the solution. Most of the elements did not interact at all as shown for Cu/Pb and no interaction was greater than the Zn/Cs interaction as summarized in Table 4. Experiments with higher concentrations (of the order of 100 ppm) demonstrate that a number of passages through the biomass drastically reduces the concentration of these elements.

TABLE 1

Biomass production by *Cladosporium cladosporioides* and *Penicillum digitatum* cultured in different medium compositions

| Medium composition | Cladosporium Cladosporioides | | Penicillium digitatum | |
|---|---|---|---|---|
| | Wet weight | Dry weight | Wet weight | Dry weight |
| Harvest after 3 days | | | | |
| Slop (10%) + sucrose (2%) | 14.9 | 1.32 | 7.5 | 0.62 |
| Slop (10%) + whey powder (1%) | 14.5 | 1.04 | 11.7 | 0.84 |
| Slop (20%) + whey powder (1%) | 15.8 | 1.01 | 13.7 | 0.97 |
| Potato-dextrose (2%) — Control | 16.2 | 0.92 | 13.4 | 0.49 |
| Harvest after 7 days | | | | |
| Slop (10%) + sucrose (2%) | 31.7 | 2.95 | 15.2 | 1.10 |
| Slop (10%) + whey powder (1%) | 28.7 | 2.61 | N.P. | N.P. |
| Slop (20%) + whey powder (1%) | 33.0 | 2.16 | 19.4 | 0.96 |
| Potato-dextrose (2%) control | 38.7 | 2.71 | 9.6 | 0.56 |

Data are g. per 200 ml culture volume; all media contained 0.5% Tween 80; 0.1% $NH_4NO_3$ was added to media containing distillery slop; N.P. = not performed

TABLE 2

Removal of elements from solutions by incubation with precultured *Cladosporium cladosporioides* Acc. no. 285712 biomass
Equivalents of 10 g biomass per liter solutions were incubated with either of several concentrations.

| Initial element content in solution (ppm) | Incubation time (min) with biomass | Element retained in solution after first incubation with biomass in ppm | | | | | |
|---|---|---|---|---|---|---|---|
| | | Ni | Cu | Zn | Cd | Pb | Cr |
| 1 | 10 | 0.25 | 0.30 | 0.55 | 0.30 | —* | — |
| | 30 | 0.25 | 0.40 | 0.35 | 0.15 | — | — |
| | 120 | 0.00 | 0.10 | 0.30 | 0.10 | — | 0.40 |
| 2 | 10 | 0.55 | 0.60 | 0.90 | 0.50 | 0.00 | — |
| | 30 | 0.50 | 0.40 | 0.75 | 0.25 | 0.00 | — |
| | 120 | 0.15 | 0.10 | 0.50 | 0.20 | 0.00 | 0.60 |
| 4 | 10 | 1.35 | 1.10 | 2.00 | 1.20 | 0.00 | — |
| | 30 | 0.95 | 0.50 | 1.40 | 0.50 | 0.00 | — |
| | 120 | 0.55 | 0.25 | 1.25 | 0.45 | 0.00 | 1.65 |
| 6 | 10 | 2.25 | 1.70 | 3.00 | 2.10 | 0.75 | — |
| | 30 | 1.55 | 0.60 | 1.70 | 0.95 | 0.15 | — |
| | 120 | 0.95 | 0.40 | 1.20 | 0.85 | 0.00 | 2.60 |
| 8 | 10 | 2.60 | 2.50 | 3.80 | 2.15 | 1.35 | — |
| | 30 | 1.90 | 0.85 | 2.25 | 1.00 | 0.55 | — |
| | 120 | 1.50 | 0.40 | 1.60 | 1.10 | 0.25 | 3.45 |
| 10 | 10 | 3.90 | 3.85 | 4.85 | 3.40 | 1.87 | — |

TABLE 2-continued

Removal of elements from solutions by incubation with precultured *Cladosporium cladosporioides*
Acc. no. 285712 biomass
Equivalents of 10 g biomass per liter solutions were incubated with either of several concentrations.

| Initial element content in solution (ppm) | Incubation time (min) with biomass | Element retained in solution after first incubation with biomass in ppm | | | | | |
|---|---|---|---|---|---|---|---|
| | | Ni | Cu | Zn | Cd | Pb | Cr |
| | 30 | 2.80 | 1.20 | 2.75 | 1.70 | 0.80 | — |
| | 120 | 2.00 | 0.70 | 2.55 | 1.50 | 0.10 | 3.75 |
| Number of incubation × min cycles required to completely remove 10 ppm from solution | | 2 × 120' | 2 × 120' | 3 × 120' | 3 × 120' | 2 × 30' | 5 × 120' |

*These tests were not performed

TABLE 3

Biosorption of one element in the presence of another element a. Biosorption of Cu in the presence of $Pb(NO_3)_2$

| $Pb(NO_3)_2$ present in the incubation solution (ppm) | Initial concentration of $CuSO_4$ (ppm) | | |
|---|---|---|---|
| | 5 | 10 | 20 |
| | $CuSO_4$ (ppm) after 2 h incubation | | |
| 0 | 0.80 | 1.40 | 3.75 |
| 5 | 0.90 | 1.55 | 3.75 |
| 10 | 0.85 | 1.40 | 3.60 |
| 20 | 0.80 | 1.55 | 3.90 | b. Biosorption of Zn in the presecnce of $CdCl_2$

| $CdCl_2$ present in the incubation solution (ppm) | Initial concentration of $ZnCl_2$ (ppm) | | |
|---|---|---|---|
| | 5 | 10 | 20 |
| | $ZnCl_2$ (ppm) after 2 h incubation | | |
| 0 | 0.90 | 2.75 | 7.20 |
| 5 | 1.05 | 3.60 | 7.90 |
| 10 | 1.20 | 3.65 | 8.90 |
| 20 | 1.45 | 4.15 | 9.45 |

TABLE 4

The removal, from incubation solution, of one element in the presence of three concentration of solutions of another (interacting) element. Summary of results as exemplified for two interaction in Table 3

| Solution | Interacting solution concentration (ppm) | Element for which removal from solution was measured | | | | |
|---|---|---|---|---|---|---|
| | | Pb | Cu | Zn | Cd | Ni |
| $Pb(NO_3)_2$ | 5 | — | NO | NO | NO | NO |
| | 10 | — | NO | NO | NO | NO |
| | 20 | — | NO | S | NO | S |
| $CuSO_4$ | 5 | NO | — | S | NO | NO |
| | 10 | NO | — | S | NO | NO |
| | 20 | NO | — | S | NO | S |
| $ZnCl_2$ | 5 | NO | NO | — | S | NO |
| | 10 | NO | NO | — | S | NO |
| | 20 | NO | NO | — | S | S |
| $CdCl_2$ | 5 | NO | NO | S | — | NO |
| | 10 | NO | NO | S | — | NO |
| | 20 | NO | NO | S | — | S |
| $NiCl_2$ | 5 | NO | NO | NO | NO | — |
| | 10 | NO | NO | NO | NO | — |
| | 20 | NO | NO | S | S | — |

No - No interaction between elements
S - slight interaction as or less than Zn/Cd interaction detailed in Table 3.

We claim:

1. A process for the substantial decrease of heavy metal concentration in industrial effluents which comprises contacting such aqueous effluent for a sufficient period of time with a fungal hyphae biomass of *Cladosporium cladosporioides* Acc. No. 285712, so as to adsorb a large percentage of such heavy metals on said biomass.

2. A process according to claim 1, wherein the heavy metal is selected from Ni, Cu, Zn, Cd, Pb, Cr and a combination of any of these, in the range of up to some tens of ppm.

3. A process as claimed in claim 2, wherein the biomass is reconditioned by the application of an aqueous solution of a carbonate or bicarbonate or by a solution of a strong mineral acid.

4. A process according to claim 1, wherein the aqueous effluent is contacted with the biomass in a stirred container.

5. A process according to claim 4, wherein the effluent is contacted with the aqueous effluent in a sequence of containers containing such biomass.

6. A system for the complete removal or substantial decrease in concentration of a heavy metal in an aqueous solution containing the same, which comprises a container containing as an active medium for the absorption of said metal a biomass comprising mainly a fungal hyphae of the fungus *Cladosporium cladosporiodies* (Fresen) de Vrie, Acc. No. 285712, Commonwealth Mycological Institute, Surrey, United Kingdom; and inlet means for contacting the aqueous solution containing the heavy metal with said biomass for an adequate period of time for such absorption; and an outlet means for separating said aqueous medium from said biomass.

7. The system of claim 6 wherein the container is provided with an inlet and an outlet means, a means for agitating the content of the container, and a means for contacting the biomass after separation of the treated aqueous medium with an aqueous solution of an acid or an alkali suited for regenerating the biomass.

8. The system of claim 7, comprising a sequence of a number of such containers, and a means for the transfer of the aqueous medium from one container to a subsequent one.

9. The system of claim 6, comprising a column containing the biomass, said column being provided with an inlet and an outlet means, and a means for introducing an aqueous solution which contains the heavy metal to be removed and for adjusting the flow rate of this solution so that a predetermined precentage of the contaminating heavy metal will be removed during the passage of said solution through the biomass in the said column.

10. The system of claim 6, wherein said system comprises an inlet means for contacting said aqueous solution containing as said heavy metal Pb, Zn, Cd, Ni, Cu, Cr, or a combination of any of these, with said biomass for an adequate period of time for absorption of said heavy metal.

* * * * *